US00PP10466P

United States Patent [19]

Wilfret

[11] Patent Number: Plant 10,466

[45] Date of Patent: Jun. 23, 1998

[54] CALADIUM PLANT CALLED "FLORIDA CALYPSO"

[75] Inventor: Gary J. Wilfret, Sarasota, Fla.

[73] Assignee: Florida Foundation Seed Producers, Inc., Greenwood, Fla.

[21] Appl. No.: 747,437

[22] Filed: Nov. 12, 1996

[51] Int. Cl.[6] ..... A01H 5/00

[52] U.S. Cl. ..... Plt./88.1

[58] Field of Search ..... Plt./88.1

[56] References Cited

PUBLICATIONS

Wilfret, Gary J. (1995) "Florida Calypso; A Multicolored Caladium for the Landscape and Containers" HortScience, vol. 30(4), p. 777, Jul. 1995.

*Primary Examiner*—James R. Feyrer
*Attorney, Agent, or Firm*—William M. Hobby, III

[57] ABSTRACT

A new, novel Caladium plant (*Caladium×hortulanum*) having enhanced tuber size, eye characteristics and disease resistant characteristics is disclosed. The new Caladium 'Florida Calypso' is further characterized by forming multiple large, heart-shaped leaves, with a bright red primary, palmate vein pattern; the red of the veins suffusing into a white central irregularly shaped blotch central to the leaf. The suffused portion is pink near the veins and progressively turns whiter toward the margins. The leaf has a solid green colored margin and contain white spots or blotches inside the margin which progressively, with greater distance from the margin, become increasingly larger mottles and striations until becoming the predominating central white to pink variegation. The leaf markings characteristically vary slightly from leaf to leaf.

1 Drawing Sheet

BACKGROUND OF THE INVENTION

A new and distinct multicolored Caladium for use as a landscape or container plant. Caladiums, grown for their colorful foliage in containers and in the landscape, are the major floricultural tuber crop grown in Florida. Over 1400 acres of caladium tubers are grown in the muck soils of central Florida and a limited acreage is planted on sandy soils in west-central Florida. Tuber production has an annual value of over seven million dollars and represents about 95% of the caladiums used worldwide for forcing in containers or in the landscape. Caladiums are planted for their variety of leaf colors, shapes, color patterns, and their ability to grow in areas of reduced light and high temperatures. One of the most popular cultivars is 'Carolyn Whorton', which has deep green leaf margins, dark red main veins, and large rose blotches. Major disadvantages of this cultivar are its susceptibility to bacterial and fungal diseases and its production of tubers with one or two predominant leaves (eyes), which usually are excised prior to planting to initiate development of lateral eyes. An improvement on this cultivar would need to incororate color, health, multiple-eyed tubers, earliness, and ease of propagation.

A caladium breeding program emphasizing bright color leaves, multiple leaf develoment, and large, good quality tubers was initiated in 1976 at the Gulf Coast Research and Education Center in Bradenton. Hybridization among commercial cultivars and selected crosses among resultant seedlings and their subsequent selection and culture on sandy and muck soils led to the development of 'Florida Calypso'. This cultivar has multicolored leaves and growth characteristics that make it suitable for forcing in containers and also can be used in the landscape in areas ranging from heavy shade to full sun.

DRAWINGS

FIG. 1 is a color photograph of a typical specimen of my new Caladium plant; and FIG. 2 is color photo of a typical specimen of tubers of the Caladium plant of FIG. 1.

SUMMARY OF THE INVENTION

The present Caladium plant (*Caladium×hortulanum*) has a unique leaf having large red veins radiating from large central red veins and has a combination of colors with rose and white blotches on the leaves as hereinafter set forth with colors based on The Royal Horticultural Society London colour chart. The plant also has unique large intact multi-segmented tubers.

Lineage: 'Florida Calypso', as seen in FIG. 1, was developed and evaluated as S84-117, and was derived from a cross between two seedlings. Lineage of 'Florida Calypso' is [S80-104 ('Carolyn Whorton'×'White Christmas')×S80-80 ('Candidum'×'Carolyn Whorton')]. Ancestry of the original parents is unknown, although 'White Christmas' is probably derived through a single gene mutation of 'Candidum'. 'Candidum' is the major white cultivar grown in the floricultural industry. It has medium-dark green leaf margins, large green main veins, finely netted green secondary veins, and white interveins. It is a tall cultivar but produces many leaves and large healthy tubers. 'White Christmas' has medium-dark green leaf margins, green main veins, and large white blotches. It is generally shorter, has a larger leaf, and does not become pink under stress as compared to 'Candidum'. Seedling S80-104 produces leaves with dark green margins, red main veins, and white and rose blotches. It is healthy but produces few leaves. Seedling S80-80 has leaves with medium green margins, red main veins, and netted venation. It produces a tuber with multiple eyes and is healthy. Tubers were propagated on a fumigated Eau-Gallie fine sand at Bradenton, Florida and were hot water treated only after observational evalutions were made from 1984 to 1986.

Asexual reproduction: The new plant was initially asexually reproduced by rooting of cuttings, by runners, and from bulb chips cut from bulbs at the Gulf Coast Research and Education Center in Bradenton.

DETAILED DESCRIPTION OF THE PLANT

Figure 1:
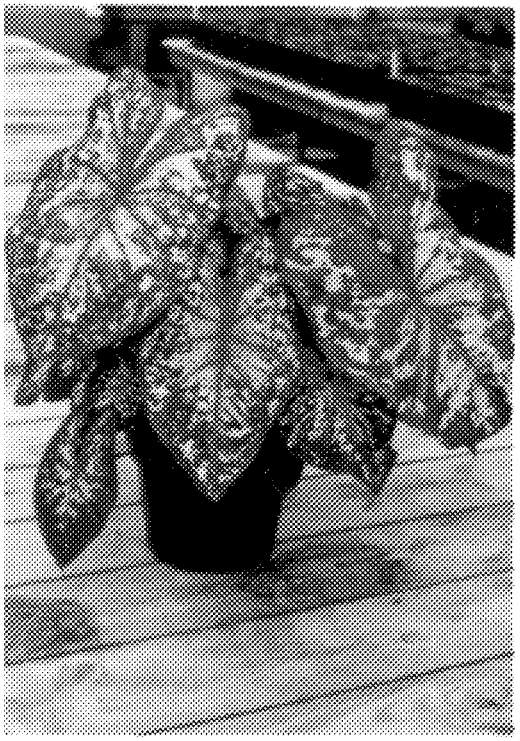

Leaves: 'Florida Calypso' produces 18 to 22 fancy leaves up to 33 cm long and 23 cm wide, with a maximum height of 82 cm after 4 months in the field as seen in FIG. 1. The color of the leaves grown in full sun, based on The Royal Horticultural Society London colour chart, is medium green (R.H.S. Green 137B). The 10 large red veins radiating from the large central red vein (R.H.S. Red 53D) are very prominent. Large rose (R.H.S. Red 55B) and white (R.H.S. Yellow White 158C) blotches of irregular shape and dimension are scattered randomly throughout the interveinal leaf surface. The rose blotches often subtend the central main vein. When grown in shady locations, the blotches often coalesce and become almost translucent. Petiole color of mature leaves is medium brown (R.H.S. Grey Brown 199B) with dark brown specks (R.H.S. Brown 200D). Young petioles can be rose-brown (R.H.S. Greyed Red 180C) with dark brown specks (R.H.S. Brown 200D). Petioles are strong and upright. Leaves are peltate, saggitate ovate, and have palmate venation.

Figure 2:
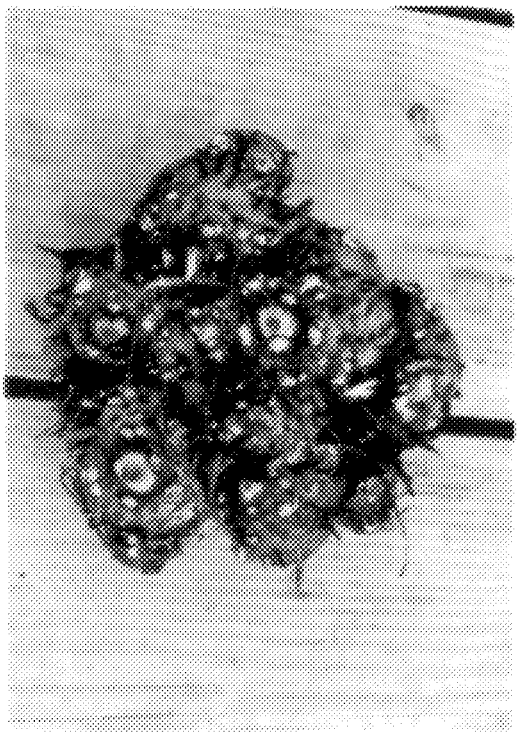

Tubers: 'Florida Calypso', has large intact tubers (>5 cm diam.) which are planted in sandy soil and grown with no shade, as seen in FIG. 2. The tubers are multisegmented but have a dominant central vegetative bud surrounded by numerous smaller buds. For optimum performance in containers, the central bud should be excised (FIG. 1). The surface of the tuber is medium brown (R.H.S. Grey Brown 199A) and the cortical area is a medium yellow (R.H.S. Yellow 11B).

Inflorescence: The flowering and reproductive organs of 'Florida Calypso' do not differ in character from other caladium plants.

Comparisons with other caladium plants: Table 1 is an evaluation of caladium cultivars grown in 4 inch containers in 1994. Table 2 is an evaluation of caladium cultivars grown in 6 inch containers in 1994. Table 3 shows Caladium tuber yields in 1991 when grown in sandy soil. The forcing of 'Florida Calypso' in containers was compared to some of the commercial caladium cultivars used for this purpose. When grown as one de-eyed No. 1 tuber (>3.8<6.4 cm diam) per 10 cm container in a glasshouse with 40% light exclusion, leaf development of 'Florida Calypso' was earlier than 'Carolyn Whorton' and similar to the other cultivars evaluated (Table 1). Plants of 'Florida Calypso' were shorter than 'Carolyn Whorton', taller than 'Candidum Jr.', or 'Florida Cardinal' and of a height similar to the remaining cultivars. The most obvious difference among the cultivars was the number of leaves, as 'Florida Calypso' produced three times as many leaves as 'Carolyn Whorton' and significantly more leaves than all of the other cultivars except for 'Florida Cardinal'. Plants were also grown in a black polypropylene shade house (30% light exclusion). Tubers were either intact or de-eyed and three No. 1 tubers were planted per 15 cm plastic pot (Table 2). 'Florida Calypso' plants were taller than 'Florida Cardinal' and 'Florida Fantasy' and similar in height to 'Florida Elise' when grown from either intact or de-eyed tubers. When 'Florida Calypso' tubers were de-eyed, the plants were about 5 cm shorter than from intact tubers. Leaf number was similar among all cultivars grown from intact tubers. When tubers were de-eyed, 'Florida Calypso' and 'Florida Cardinal' produced more leaves than the other cultivars. Leaves of 'Florida Calypso' were longer and wider than 'Florida Elise' and 'Florida Fantasy'. Petiole length followed a pattern similar to plant height. Although data were not recorded on time of leaf development, it was apparent that leaves of 'Florida Calypso' unfurled earlier than those of the other cultivars.

'Florida Calypso' was compared to several commercial cultivars for tuber production on fumigated sandy soil at Bradenton, Fla. Total weight, as seen in Table 3, of tubers dug of 'Florida Calpyso' and 'Florida Cardinal' were similar and both cultivars produced a similar number of marketable tubers. Tuber weight was greater than the other cultivars except 'Candidum' and 'Florida Elise'. 'Florida Cardinal' and 'Florida Elise' produced more mammoth tubers than 'Florida Calypso' but yielded a similar number of jumbo tubers.

'Florida Calypso' produced significantly more marketable tubers than 'Carolyn Whorton', 'Candidum Jr.', 'Florida Fantasy', and 'Red Flash'. Weights of tubers dug were greater with 'Florida Calypso' than 'Carolyn Whorton', 'Candidum Jr.', and 'Florida Fantasy'. The production index, which is determined by number of tubers in each grade times a tuber value, showed that 'Florida Calypso' is equivalent to 'Candidum' and 'Fire Chief' in value return and yielded greater return than all the other cultivars. Tubers of 'Florida Calypso' have been grown in the muck soils in Lake Placid, Fla. and tuber yields were greater than those of 'Carolyn Whorton'. Plants of 'Florida Calypso' were some of the earliest to be visible in the field and also were some of the earliest to collapse in the fall. The tubers were not high crowned, with a height to diameter ratio of approximately 1:2. Tubers were healthier than 'Carolyn Whorton' and similar in yield to 'Candidum'.

'Florida Calypso' is intended for forcing in containers of 10 to 20 cm diameter and can be grown from shady to full sun locations in the landscape. Tubers should be de-eyed when planted in 10 to 15 cm pots, but the main vegetative buds should not be excised before planting in large containers. Best foliage color and definition is obtained when plants are grown with 35% to 40% light exclusion. 'Florida Calypso' does not have the uniform rose blotches of 'Carolyn Whorton' but has a mixture of rose and white blotches. Although extensive research and evaluations have been performed on small acreages of this cultivar, growers are encouraged to plant only limited quantities of 'Florida Calypso' until they have gained experience in its production. Standard postharvest treatment of tubers is recommended and preplant hot water treatment of tubers is encouraged to prolong the life of the tubers.

TABLE 1

Evaluation of caladium cultivars grown in 4 inch containers in 1994.

| Cultivar[z] | Number Days to First Leaf | Number Days to 5 Leaves | Plant Height (cm) | Number Leaves (8 wks) |
|---|---|---|---|---|
| Florida Calypso | 27.8 | 33.4 | 33.0 | 33.6 |
| Carolyn Whorton | 30.2 | 48.2 | 42.9 | 11.0 |
| Candidum | 25.2 | 36.6 | 33.0 | 17.5 |
| Candidum Jr. | 29.8 | 35.1 | 27.0 | 22.9 |
| Florida Cardinal | 29.5 | 35.1 | 27.2 | 29.1 |
| Florida Elise | 30.1 | 36.0 | 34.9 | 24.6 |
| White Christmas | 29.2 | 35.5 | 31.8 | 16.2 |
| LSD (P = 0.05) | 4.1 | 4.8 | 3.6 | 4.9 |

[z]One #1 de-eyed tuber/pot; grown under 40% shade.

TABLE 2

Evaluation of caladium cultivars grown in 6 inch containers in 1994.

| Cultivar[z] | Plant Height (cm) | | Number Leaves | |
|---|---|---|---|---|
| | Intact | De-Eyed | Intact | De-Eyed |
| Florida Calypso | 47.8 | 42.5 | 21.6 | 42.2 |
| Florida Cardinal | 35.0 | 34.6 | 25.0 | 47.7 |
| Florida Elise | 44.5 | 39.3 | 21.5 | 39.2 |
| Florida Fantasy | 34.6 | 28.8 | 21.7 | 31.7 |
| LSD (P = 0.05) | | 3.4 | | 5.6 |

| Cultivar | Leaf Length (cm) | | Leaf Width (cm) | | Petiole Length (cm) | |
|---|---|---|---|---|---|---|
| | Intact | De-Eyed | Intact | De-Eyed | Intact | De-Eyed |
| Florida Calypso | 34.3 | 27.7 | 22.0 | 18.9 | 38.7 | 34.1 |
| Florida Cardinal | 30.3 | 26.0 | 19.9 | 17.3 | 27.3 | 26.3 |
| Florida Elise | 28.6 | 22.0 | 19.5 | 15.3 | 36.4 | 33.0 |
| Florida Fantasy | 27.5 | 22.1 | 19.7 | 17.1 | 31.8 | 24.6 |
| LSD (P = 0.05) | | | 3.8 | | 2.2 | 3.6 |

[z]Three - #1 tubers/pot; grown under 30% shade.

TABLE 3

Caladium tuber yields in 1991 when grown in sandy soil.

| Cultivar | Number Tubers By Grade | | | | | Total Tuber |
|---|---|---|---|---|---|---|
| | Mammoth | Jumbo | #1 | #2 | Total | Weight |
| Florida Calypso | 0.8 | 5.5 | 8.3 | 3.0 | 17.6 | 1470 |
| Carolyn Whorton | 0 | 0.3 | 5.3 | 7.5 | 13.1 | 595 |
| Candidum | 1.0 | 3.3 | 7.5 | 6.0 | 17.8 | 1190 |
| Candidum Jr. | 0 | 1.5 | 3.8 | 10.5 | 15.8 | 792 |
| Florida Cardinal | 4.3 | 9.5 | 3.1 | 1.3 | 18.3 | 1610 |
| Florida Elise | 2.5 | 7.3 | 6.2 | 2.0 | 18.0 | 1175 |
| Florida Fantasy | 0 | 0.3 | 6.8 | 8.8 | 15.8 | 881 |
| LSD (P = 0.05) | 1.3 | 3.1 | 3.2 | 2.6 | 2.8 | 410 |

[z]Mean of 4 replications of 16 tuber chips (2 cm) per replication (0.0005 Acres)

TABLE 4

Caladium tuber yields in 1993 when grown in a sandy soil.

| Cultivar | Number Tubers By Grades | | | | | Total Tuber Weight | Production Index[y] |
|---|---|---|---|---|---|---|---|
| | Mammoth | Jumbo | #1 | #2 | Total | (g) | |
| Florida Calypso | 2.3 | 6.5 | 14.5 | 12.8 | 36.1 | 2762 | 86.2 |
| Carolyn Whorton | 0 | 3.5 | 10.3 | 8.5 | 22.3 | 1390 | 43.1 |
| Candidum | 1.8 | 8.8 | 15.5 | 14.0 | 40.1 | 2930 | 94.6 |
| Candidum Jr. | 0 | 1.3 | 12.3 | 5.8 | 19.4 | 865 | 35.4 |
| Florida Fantasy | 0.3 | 2.5 | 10.0 | 16.0 | 28.8 | 1438 | 48.0 |
| Fire Chief | 2.0 | 6.3 | 20.8 | 11.3 | 40.4 | 3075 | 94.1 |
| Red Flash | 2.6 | 5.5 | 13.8 | 5.5 | 27.4 | 2470 | 76.5 |
| White Christmas | 1.0 | 3.3 | 23.0 | 12.8 | 40.1 | 2540 | 80.0 |
| LSD (P = 0.05) | 1.2 | 2.8 | 3.4 | 3.6 | 4.2 | 780 | 14.3 |

[z]Yields are mean of 4 replications of 30 tuber chips (2 cm) per replication (0.0007 acres/plot).

[y]Production index = (1 × # No. 2) + (2 × # No. 2) + (4 × # Jumbo) + (8 × # Mammoth) tubers.

I claim:

1. A new and distinct variety of Caladium plant called 'Florida Calypso', substantially as herein illustrated and described, characterized by its unique combination of leaf colors.

* * * * *